United States Patent [19]

Raible

[11] Patent Number: 5,217,689
[45] Date of Patent: Jun. 8, 1993

[54] BLOOD OXYGENATION SYSTEM

[75] Inventor: Donald A. Raible, Santa Ana, Calif.

[73] Assignee: Baxter International Inc., Deerfield, Ill.

[21] Appl. No.: 428,270

[22] Filed: Oct. 26, 1989

[51] Int. Cl.$^5$ .................. A61M 1/14; A61M 1/18
[52] U.S. Cl. .................. 422/46; 422/48; 128/DIG. 3; 261/DIG. 28; 55/16; 55/158; 210/646; 210/321.81; 210/321.83; 210/321.89
[58] Field of Search ............ 422/46, 48; 128/DIG. 3; 261/DIG. 28; 55/16, 158; 210/646, 321.79, 321.81, 321.83, 321.88, 321.89

[56] References Cited

U.S. PATENT DOCUMENTS

| | | | |
|---|---|---|---|
| 3,422,008 | 1/1969 | McLain | 210/646 |
| 3,536,611 | 10/1970 | deFilippi et al. | 210/646 |
| 3,769,162 | 10/1973 | Brumfield | 128/DIG. 3 |
| 3,794,468 | 2/1974 | Leonard | 422/48 |
| 3,856,475 | 12/1974 | Marx | 55/16 X |
| 4,188,360 | 2/1980 | Kurata | 422/46 |
| 4,272,373 | 6/1981 | Stenberg et al. | 422/48 X |
| 4,280,981 | 7/1981 | Harnsberger | 422/46 |
| 4,306,018 | 12/1981 | Kirkpatrick | 261/DIG. 28 X |
| 4,352,736 | 10/1982 | Ukai et al. | 55/158 X |
| 4,620,965 | 11/1986 | Fukusawa et al. | 422/46 |
| 4,639,353 | 1/1987 | Takemura et al. | 422/46 |
| 4,645,645 | 2/1987 | Martinez et al. | 422/46 |
| 4,656,004 | 4/1987 | Stewart | 422/46 |

FOREIGN PATENT DOCUMENTS

| | | |
|---|---|---|
| 0003495 | 12/1978 | European Pat. Off. . |
| 0103899 | 9/1983 | European Pat. Off. . |
| 0380307 | 1/1990 | European Pat. Off. . |
| 139562 | 12/1986 | Japan . |
| 1419551 | 12/1975 | United Kingdom .................. 422/46 |

OTHER PUBLICATIONS

"Pumpless Extracorporeal Oxygenation of the Blood through a Hollow Fiber Oxygenator", vol. XXXI Trans Am Soc Artif Intern Organs, 1985, pp. 363–366.

Primary Examiner—Lynn Kummert
Attorney, Agent, or Firm—Bruce M. Canter; Loyal M. Hanson

[57] ABSTRACT

A blood oxygenation system includes an oxygenator for oxygenating blood and a heat exchanger for regulating blood temperature. The heat exchanger includes a heat exchange coil that provides a flow path for a heat exchange media, the heat exchange coil is configured to define a heat exchange zone, and the oxygenator is disposed in heat transfer relationship with the heat exchange zone in order to transfer heat between the heat exchange coil and the oxygenator. The heat exchange coil may at least partially circumscribe the oxygenator and, preferably, be helically shaped and disposed coaxially over a membrane oxygenator. In one embodiment, single or multiple hollow fiber strands are wound onto a small diameter center core so that the fiber segments provide spiralling helical blood-flow pathways which increase oxygen/carbon dioxide exchange by secondary flow paths.

12 Claims, 2 Drawing Sheets

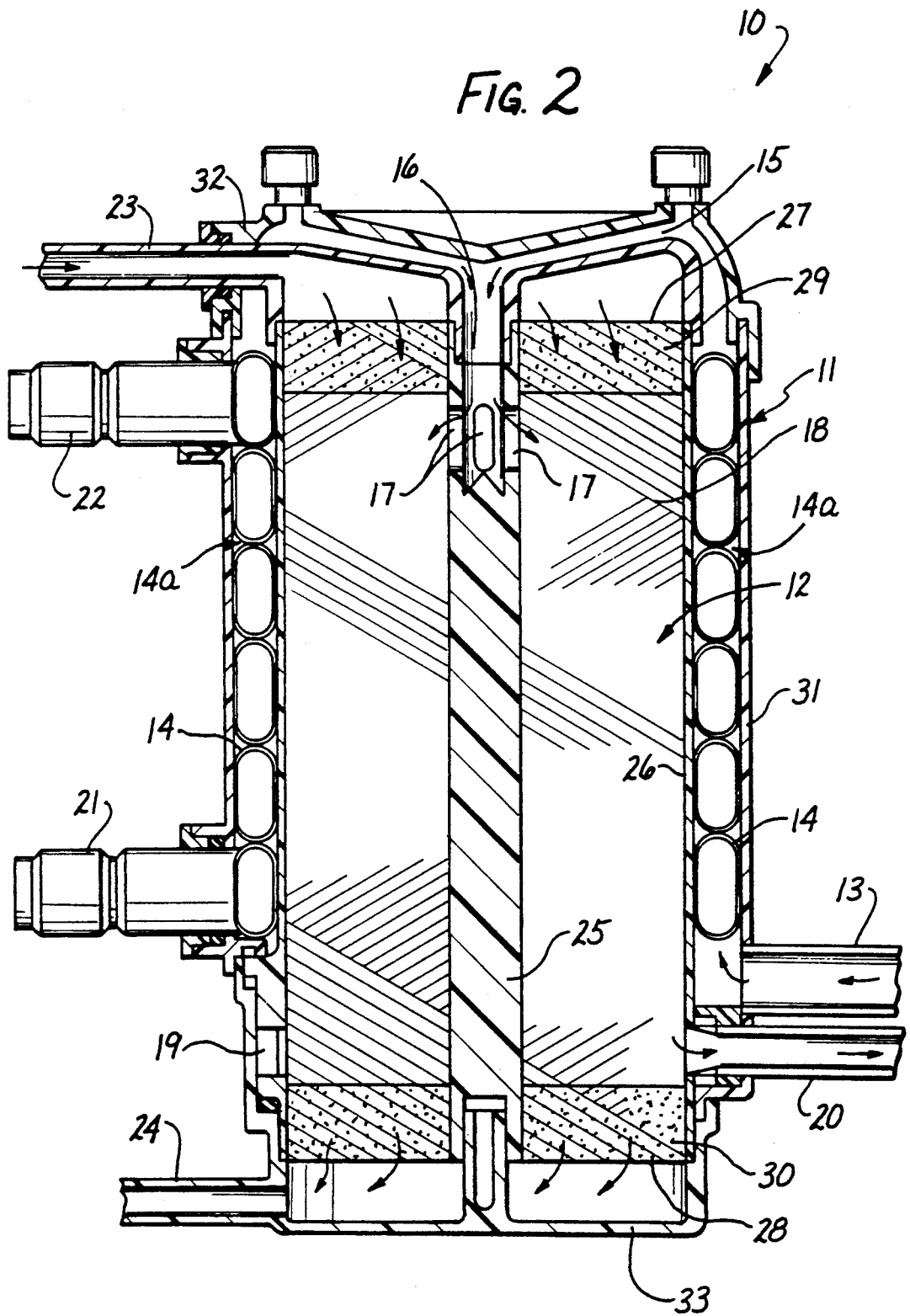

BLOOD OXYGENATION SYSTEM

BACKGROUND OF THE INVENTION

1. Technical Field

This invention relates generally to medical equipment, and more particularly to a blood oxygenation system.

2. Background Information

A blood oxygenation system serves as the patient's lungs during such procedures as open heart surgery. It includes an oxygenation module or oxygenator that replaces carbon dioxide in the blood with a fresh supply of oxygen and a separate heat exchanger that regulates blood temperature. Thus, it is an important component in various surgical procedures and the details of design demand attention.

Some oxygenators employ a bundle of hollow fibers as conduits for a flow of oxygen. They are formed from microporous membrane material and as a result some of the oxygen flows through the pores to blood pumped past the fiber exteriors while carbon dioxide from the blood flows in the opposite direction to join the flow of oxygen as it is vented. That process oxygenates the blood, and the membrane oxygenator described in U.S. patent application Ser. No. 056,135 filed May 29, 1987 provides an example.

Similarly, the heat exchanger may employ a heat exchange coil as a conduit for a flow of temperature regulated water. As the blood flows past the exterior surface of the heat exchange coil, heat transfers through the coil between the blood and the water to regulate blood temperature. The heat exchanger described in Raible U.S. Pat. No. 4,428,934 is an example and that patent is incorporated for the details provided.

There are certain drawbacks with existing membrane oxygenation systems, however, such as the priming volume that the system requires as well as the efficiency of the oxygen and carbon dioxide exchange accompanying the use of separate heat exchange and oxygenation modules and the relatively inefficient membrane gas exchange modules. Those things can, in turn, result in a larger system with higher priming volumes and fabrication costs, and the need for higher pumping pressure with the attendant risk of blood damage. Consequently, it is desirable to have an oxygenation system that alleviates those concerns.

Summary of the Invention

This invention solves the problems outlined above by providing a system having a heat exchanger so configured that it can heat the blood in the oxygenation module as well as the blood in the heat exchange module. More specifically, the heat exchanger includes a heat exchange coil that is arranged to define a heat exchange zone or space that the heat exchange coil at least partially surrounds, the oxygenator being located in heat transfer relationship with the heat exchange zone, preferably coaxially within it. As a result, heat transfer occurs while the blood flows through the oxygenation module as well as while it flows past the heat exchange coil, and that achieves a more efficient regulation of blood temperature.

With that construction, the heat exchange coil can be shorter and the surface area can be decreased. As a result, the volume of the blood flow path can be reduced so that less blood is needed for priming. A more compact system results. Less expensive fabrication costs are realized, and pumping pressure with the inherent blood damage is reduced.

Generally, a blood oxygenation system constructed according to the invention includes a heat exchanger and means for oxygenating blood that are arranged to enable the passage of blood through them in order to oxygenate the blood and regulate blood temperature. According to a major aspect of the invention, the heat exchanger includes conduit means for providing a flow path for a heat exchange media, the conduit means is configured to define a heat exchange zone, and the means for oxygenating blood is disposed in heat transfer relationship with the heat exchange zone.

In one embodiment, the conduit means at least partially circumscribes the oxygenation module or oxygenator (i.e., the means for oxygenating blood). Preferably, the conduit means includes a heat exchange coil that is disposed coaxially around the oxygenation module, and the oxygenation module/heat exchanger combination may take the form of a membrane oxygenator.

The foregoing and other objects and features of the invention and the manner of attaining them will become apparent and the invention itself will be best understood by reference to the following description taken in conjunction with the accompanying illustrative drawings.

BRIEF DESCRIPTION OF THE DRAWINGS

FIG. 2 is a cross sectional view of the blood oxygenation system.

DESCRIPTION OF THE PREFERRED EMBODIMENTS

Figure 1:
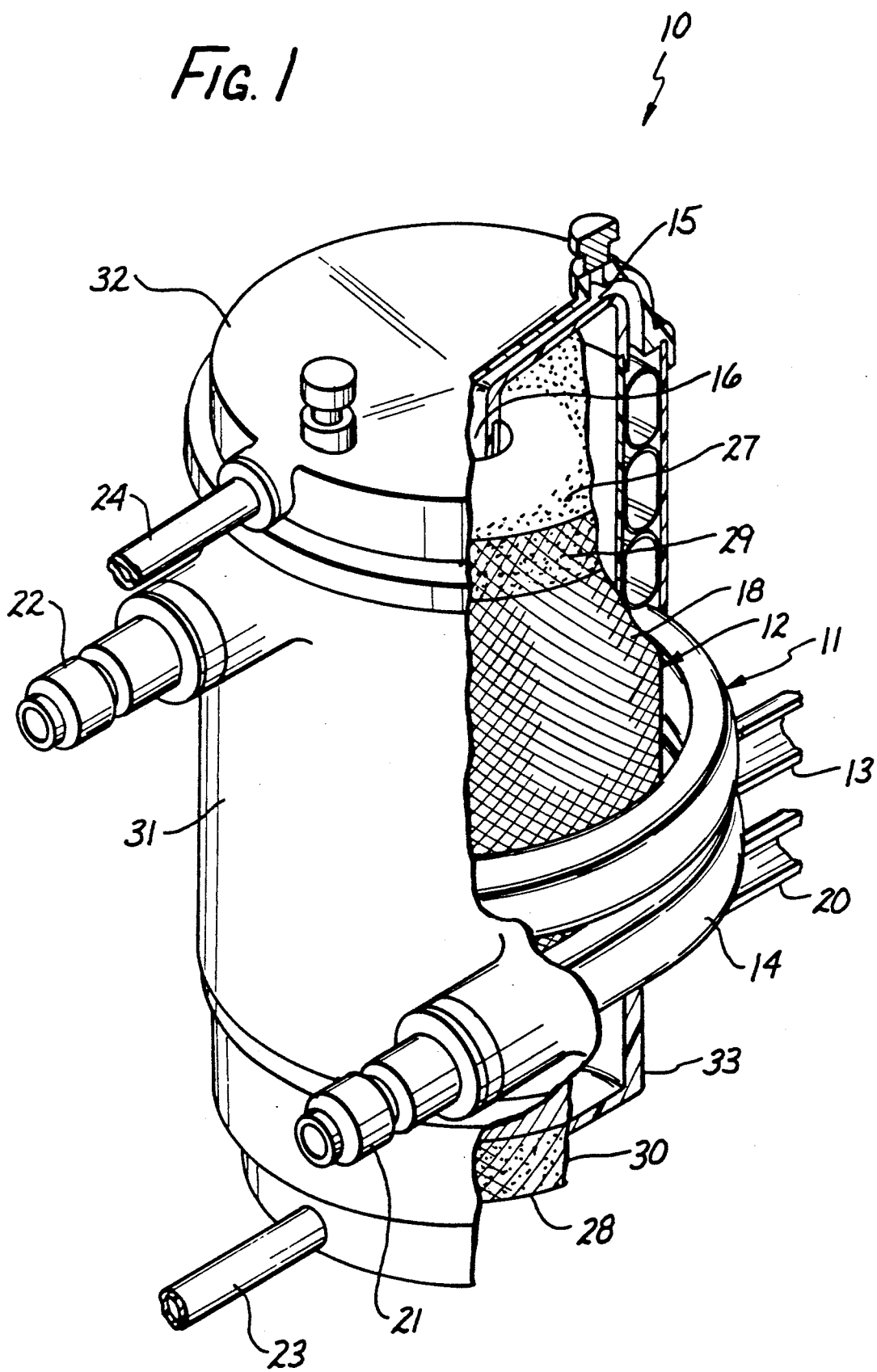
FIG. 1 of the drawings is a perspective view of a blood oxygenation system constructed according to the invention.

Referring now to the drawings, there is shown a blood oxygenation system 10 that includes a heat exchange module or heat exchanger 11 disposed coaxially around an oxygenation module or oxygenator 12 that serves as means for oxygenating blood. The heat exchanger 11 and the oxygenator 12 are arranged to enable the passage of blood through them in order to both oxygenate the blood and regulate blood temperature. They are arranged so that blood flows first through one and then the other, and as that happens, they operate conventionally in some respects as subsequently discussed to oxygenate the blood and regulate blood temperature.

Blood from a patient flows under gravity and then is pumped under pressure into a blood inlet 13 and thereby into the heat exchanger 11, a suitable known type of pump (not shown) providing the pumping action needed. Next, the blood flows past the exterior of a heat exchange coil 14 in the heat exchanger 11 that serves as conduit means for providing a flow path for a heat exchange media subsequently described, the blood flowing in a helical path around the oxygenator 12 through a passage 14a (FIG. 2) formed by adjacent turns of the heat exchange coil 14. As it does so, it exchanges heat with the heat exchange coil 14 and thereby with the heat transfer media that is flowing through the heat exchange coil 14. Thereafter, the blood passes through a passage 15 into the oxygenator 12 (FIGS. 1 and 2).

Once in the oxygenator 12, the blood flows through a passage 16 to ports 17 (FIG. 2) that open radially outwardly toward a fiber bundle 18, and then through the ports 17 into the fiber bundle 18. Next, the blood flows radially outwardly and downwardly through the fiber bundle 18 to a collection space 19 (FIG. 2) as it is oxygenated along the way by exchanging oxygen and carbon dioxide with a flow of oxygen through the fiber bundle 18. Then the blood flows from the collection space 19 out a blood outlet 20 (FIGS. 1 and 2) and back to the patient.

Meanwhile, a heat transfer media, such as water, flows under pressure into a water inlet 21 (FIGS. 1 and 2) and thereby into the heat exchange coil 14. The water then flows through the heat exchange coil 14 and back out through a water outlet 22, exchanging heat with the heat exchange coil 14 along the way (and thereby the blood) in order to regulate the temperature of the blood. As that occurs, a flow of oxygen or oxygen-rich gas from a suitable source such as a tank of compressed oxygen (not shown) flows under pressure into an oxygen inlet 23 (FIGS. 1 and 2), through the fiber bundle 18, and back out through an oxygen outlet 24, exchanging oxygen and carbon dioxide with the blood along the way in order to oxygenate the blood.

Thus, various aspects of the blood oxygenation system 10 operate somewhat conventionally. However, according to a major aspect of the invention, the conduit means (i.e., the heat exchange coil 14) is configured to define a heat exchange zone, and the means for oxygenating blood (i.e., the oxygenator 12) is disposed in heat transfer relationship with the heat exchange zone. In other words, the heat exchange coil 14 is so arranged that it defines a space (i.e., the heat exchange zone) disposed inwardly of the heat exchange coil 14, and the oxygenator 12 is located in heat transfer relationship to the heat exchange zone so that heat can not only transfer between the blood and the heat exchange coil 14, but also between the oxygenator 12 and the heat exchange coil 14.

The heat exchange zone for the system 10 is the cylindrically shaped space disposed inwardly of the heat exchange coil 14 (i.e., the space occupied by the oxygenator 12). Preferably, the oxygenation means is disposed substantially fully within the heat exchange zone as illustrated for the system 10 in order to effect the most efficient transfer of heat between the oxygenator 12 and the heat exchange coil 14. Preferably, the heat exchange coil 14 is helically configured as illustrated and so disposed that it coaxially circumscribes the oxygenator 12 for that purpose. However, it is within the broader inventive concepts disclosed to have the oxygenator 12 disposed partially within the heat exchange zone and even outside of but adjacent to the heat exchange zone where heat transfer can take place.

Consider, for example, the case where the water or other heat exchange medium flowing in the heat exchange coil 14 supplies heat to the blood. In that case, heat flows from the heat exchange medium to the heat exchange coil 14 and from there to the blood as the blood flows through the passage 14a past the heat exchange coil 14. But, heat also flows inwardly from the heat exchange coil 14 toward the heat exchange zone occupied by the oxygenator 12. As a result, the oxygenator 12 is heated by the inwardly flowing heat instead of that heat simply dissipating so that there is less loss of heat from the blood as the blood passes through the oxygenator 12.

Consequently, the heat exchange coil 14 need not transfer as much heat directly to the blood as would otherwise be required. Instead, the heat exchange coil 14 forms what can be called an oven in which the oxygenator 12 is disposed so that heat from the heat exchange medium is used more efficiently. The heat exchange coil 14 is shorter and the use of ribs is eliminated. The volume of the blood flow path is reduced. Less blood is needed for priming. A more compact system results Less expensive fabrication costs are realized, and pumping pressure and blood damage is reduced.

Considering the oxygenator 12 in further detail, the fiber bundle 18 is formed on a core 25 of suitable material such as a thermoplastic material (FIG. 2). The core 25 may measure about one centimeter in diameter and about fifteen centimeters long, with the fiber bundle 18 being formed to have a diameter of about seven centimeters. Of course, those dimensions are not critical and they may vary significantly depending on the application, the oxygenation system 10 representing an infant oxygenator system that is somewhat smaller than pediatric and adult oxygenator systems.

The fiber bundle 18 may be formed by helically winding a single or multiple strands of a known type of hollow fiber back and forth from end to end on the core 25 to form many layers of the single strand around the core. The strand may, for example, be formed from a microporous membrane material, such as a microporous polypropylene material having a 200–500 micron inside diameter. It may be wound on the core 25 at various angles of crossing hollow fibers using a filament winder such as the COBRA model winder available from Dura Wound of Washougal, Wash.

After the single or multiple strands of hollow fiber membrane are wound onto the core 25 to form single or multiple strand windings, the single or multiple strand windings are placed within a cylindrical sleeve (e.g., one formed of a thermoplastic material) as a first step in forming a housing 26 for the fiber bundle 18 (FIG. 2). Next, a portion of the single or multiple strand windings at either end of the sleeve is potted by known means, such as with a polyurethane type potting material. Then, a portion of the sleeve and the potted single or multiple strand windings are cut off at either end of the sleeve generally perpendicular to the core 25 to result in the housing 26 being disposed coaxially over the fiber bundle 18 and the fiber bundle 18 extending to faces 27 and 28 at potted ends 29 and 30.

That construction results in the single strand being cut into many fiber segments so that the fiber bundle 18 includes layers of fiber segments that extend along helical paths between the exposed faces 27 and 28, each fiber segment having an open end at each, of the faces 27 and 28. Oxygen flowing into the inlet 23 passes into the open ends of the fiber segments at the potted surface or face 27, downwardly through each of the helically wound fiber segments, out the open ends at the potted surface or face 28, and then out of the outlet 24. Meanwhile, blood flowing through the passage 16, passes through the ports 17 into the fiber bundle 18. There, it disperses radially outwardly and downwardly under pressure and by capillary action through fine spaces between the fiber segments, flowing along outwardly spiralling, helical paths of hollow fiber membrane surfaces which are wound around the core 25 to the collection space 19 as it is oxygenated along the way. That results in a longer flowpath that increases contact with the outside surface of the fiber segments for better oxygen and carbon dioxide transfer. In that regard, the spiral-shaped fluid pathway may vary according to the various filament winding angles utilized when winding a single fiber strand onto the core 25.

The heat exchanger coil 14 utilizes a tube arranged in a helical configuration to fit coaxially over the housing 26. It may be formed of a metal alloy and, preferably, have a smooth exterior, smooth in the sense that ribs are no included for increased surface area. In addition, it has a cross-sectional shape such that the passage 14a is formed between adjacent turns of the heat exchanger coil 14, the housing 26, and an outer housing 31 disposed coaxially over the heat exchanger coil 14 (FIGS. 1 and 2).

The oxygenator system 10 may be assembled by placing the oxygenator 12 within the heat exchanger 11 and then adding a cap structure 32 and a base structure 33 composed of a thermoplastic or other suitable material. Those components are fabricated according to known techniques to provide the passages and various inlet and outlets illustrated, and they may be bonded together in the assembly shown according to known techniques.

Thus, the invention provides a system having a heat exchanger so configured that it can heat the blood in the oxygenator as well as the blood in the heat exchanger. The heat exchanger includes a heat exchange coil that is arranged to define a heat exchange zone, the oxygenator is located in heat transfer relationship with the heat exchange zone, preferably coaxially within it, and, as a result, heat transfers between the oxygenator and the heat exchange coil to achieve a more efficient regulation of blood temperature.

Although an exemplary embodiment of the invention has been shown and described, many changes, modifications, and substitutions may be made by one having ordinary skill in the art without necessarily departing from the spirit and scope of the invention.

What is claimed is:

1. A blood oxygenation system, comprising:
   oxygenation means disposed coaxially within a first housing, including gas inlet and gas outlet means for transporting gas through the interior of the oxygenation means;
   heat exchanging means surrounding the first housing and including a conduit means for providing a flow path for a heat exchange media and including inlet means and outlet means for the heat exchange media;
   the conduit means at least partially circumscribing the oxygenation means and defining a heat exchange zone for heating the oxygenation means;
   a second housing surrounding the heat exchanging means and having blood inlet means and blood outlet means;
   the second housing defining a first blood flow path for receiving blood from the blood inlet means and permitting heat exchange between the heat exchanging means and the blood within the first blood flow path; and
   a second blood flow path centrally disposed within the oxygenation means, for receiving blood from the first blood flow path, to transmit blood radially outward form said oxygenation means, through the heat exchange zone, and out the blood outlet means.

2. A system as recited in claim 1, wherein the conduit means includes a heat exchange coil.

3. A system as recited in claim 1, wherein the heat exchanging means is disposed coaxially over the means for oxygenating blood.

4. A system as recited in claim 3, wherein the heat exchanging means comprises a coil of flattened piping.

5. A system as recited in claim 1, wherein the means for oxygenating blood includes a membrane oxygenation module.

6. A system as recited in claim 5, wherein the membrane oxygenation module is disposed at least partially within the heat exchange zone.

7. A system as recited in claim 6, wherein the conduit means includes a heat exchange coil disposed coaxially over the membrane oxygenation module.

8. A system as recited in claim 6, wherein the membrane oxygenation module includes a bundle of hollow fibers which are filament wound over one another at various degrees of angle, which membrane oxygenation module is configured to pass a flow of oxygen through the fibers and the flow of blood past the outside surface of the fibers for purposes of oxygenating the blood.

9. A system as recited in claim 8, wherein the conduit means includes a heat exchange coil disposed coaxially over the bundle of hollow fibers.

10. A blood oxygenation system, comprising:
    an oxygenation module consisting of a bundle of hollow fibers which are filament wound over each other at various degrees of angle;
    a first housing surrounding said oxygenation module the housing defining a gas inlet means for carrying a first gas through the hollow fibers and a gas outlet means for carrying a second gas away from the hollow fibers;
    heat exchanging means having fluid inlet means and fluid outlet means for transmitting heat transfer media therethrough, the heat exchanging means surrounding the first housing to exchange heat with the oxygenation module;
    a second housing surrounding the heat exchanging means and having blood inlet means for receiving blood and defining a blood path for transmitting blood past the heat exchanging means to exchange heat with the blood and for transmitting the blood to the oxygenation module;
    a blood flow path within the oxygenation module, for passing a flow of blood radially outward from the oxygenation module and past the outside surface of the fibers for the purpose of exchanging gases with the oxygenation module; and
    the second housing further having blood outlet means for carrying oxygenated blood away from the oxygenation module.

11. A system as recited in claim 10, wherein the heat exchanging means comprises flattened piping.

12. A blood oxygenating system, comprising:
    a fiber bundle having layers of hollow fibers extending between opposite ends of the fiber bundle;
    a first housing surrounding the fiber bundle;
    means for conducting oxygen to one of the opposite ends of the fiber bundle and from the other one of the opposite ends in order to enable the oxygen to flow through the fibers;
    a heat exchange coil surrounding the first housing and in heat exchange relationship with the fiber bundle;
    the heat exchange coil including inlet and outlet means for heat exchange media;
    a second housing surrounding the heat exchange coil and partially defining a flow path over the heat exchange coil in order to enable blood to flow past the heat exchange coil for purposes of regulating blood temperature;

inlet blood flow means for introducing blood to the flow path;

means for conducting blood between the blood flow path and the fiber bundle in order to enable the blood to flow around and between the fibers n the fiber bundle for oxygenation thereof; and outlet blood flow means for transporting oxygenated blood away from the blood oxygenating system.

* * * * *